United States Patent [19]

Flask et al.

[11] Patent Number: 5,378,993
[45] Date of Patent: Jan. 3, 1995

[54] LIQUID SENSING CIRCUIT

[75] Inventors: Robert J. Flask, Dayton; Charles E. Warner, Troy, both of Ohio

[73] Assignee: Premark FEG Corporation, Troy, Ohio

[21] Appl. No.: 169,624

[22] Filed: Dec. 20, 1993

[51] Int. Cl.⁶ ........................................... G01R 27/26
[52] U.S. Cl. ................... 324/663; 134/57 D
[58] Field of Search ............... 73/61.43, 61.41, 61.61; 324/663, 667, 681; 137/5; 134/57 D

[56] References Cited

U.S. PATENT DOCUMENTS

| | | | |
|---|---|---|---|
| 3,897,798 | 8/1975 | De Vale | 137/5 |
| 4,323,092 | 4/1982 | Zabel | 137/3 |
| 4,657,670 | 4/1987 | Newton | 137/93 |
| 4,733,798 | 3/1988 | Brady et al. | 137/5 |
| 4,751,842 | 6/1988 | Ekrann et al. | 324/663 X |
| 4,867,193 | 9/1989 | Hayashi et al. | 137/93 |
| 5,017,879 | 5/1991 | Lucas et al. | 324/663 |
| 5,038,807 | 8/1991 | Bailey et al. | 134/57 D |
| 5,056,542 | 10/1991 | Reinhard | 134/57 D |
| 5,131,419 | 7/1992 | Roberts | 134/57 D |
| 5,187,444 | 2/1993 | Kumada et al. | 324/663 |

FOREIGN PATENT DOCUMENTS

| | | | |
|---|---|---|---|
| 2458055 | 6/1976 | Germany | 324/663 |
| 193343 | 11/1984 | Japan | 324/663 |

*Primary Examiner*—Thomas P. Noland
*Assistant Examiner*—Joseph W. Roskos
*Attorney, Agent, or Firm*—Thompson, Hine and Flory

[57] ABSTRACT

The invention is a device that senses the presence of detergent, sanitizer, or rinse agent in chemical feed tubes. More specifically, the device is a non-invasive chemical sensor which alleviates any need for direct contact with fluid or extra connections in the chemical feed tubes.

4 Claims, 1 Drawing Sheet

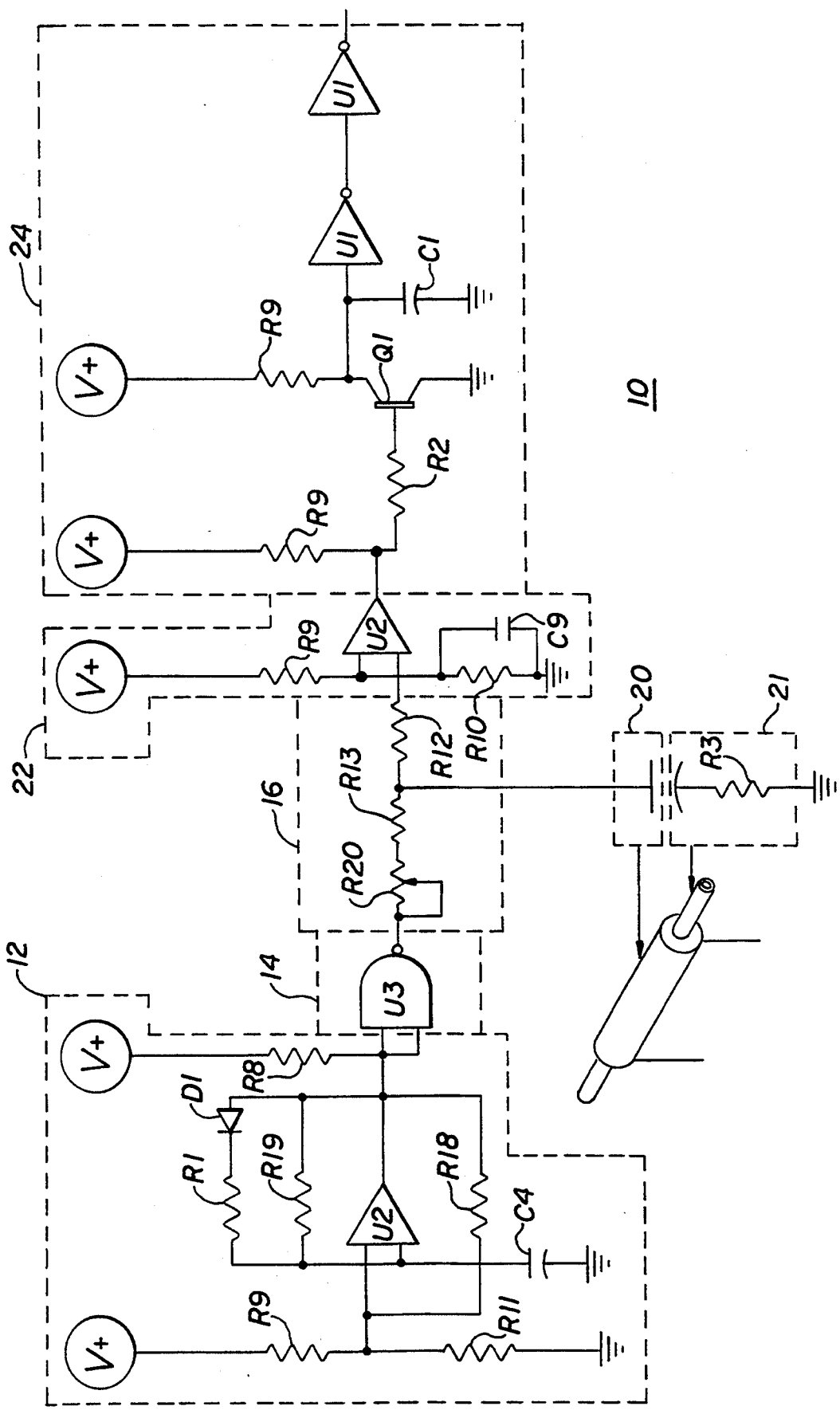

LIQUID SENSING CIRCUIT

BACKGROUND OF THE INVENTION

1. Field of the Invention

This invention relates to a device that senses the presence of detergent, sanitizer, or rinse agent in chemical feed tubes. More specifically, the invention is directed to a non-invasive chemical sensor which alleviates any need for direct contact with fluid or extra connections in the feed tubes.

2. Description of Related Art

U.S. Pat. No. 4,733,798 to Brady et al. appears to disclose a ware washing machine and an electrodeless conductive cell 12 which monitors the conductivity of the ware washing solution. Additionally, a controller is described which activates in response to the difference between the measured concentration and the actual concentration.

However, this patent does not include a sensor sensing the presence of chemicals such as detergent, sanitizer or rinse agent. Accordingly, there still exists, in this industry, a need for a liquid sensing circuit which operates in a manner that particularly improves the performance, efficiency and economy of ware washing machines, and to simplify installation, operation and maneuverability of such circuits.

SUMMARY OF THE INVENTION

The chemical sensor of the present invention is a separate unit which senses the presence of detergent, sanitizer, or rinse agent in chemical feed tubes of a dishwasher or ware washer. The sensor is non-invasive, thereby alleviating the need for any direct contact with liquid or extra connections in the feed tubes.

The chemical sensor works by sensing the change in capacitance that occurs when the fluid is introduced inside the chemical feeders. Being non-invasive, the fluid passes through a tubular shaped sensor acting as one electrode of the capacitor. The introduction of fluid in the tube causes an increase in capacitance due to a dielectric change in comparison to air. The path to ground is provided by the fluid via AC coupling. The fluid also has a resistance which appears to be in series with the capacitor. Therefore, the feed tube, the chemical and earth ground form a capacitor and resistor network.

The sensor is sensitive to both the capacitance and the resistance of the fluid. The sensor circuit is designed to operate with ionic or low resistance fluids such as bleach, detergent, or rinse aid. High resistance fluids such as deionized water will not be properly sensed.

OBJECTS OF THE INVENTION

It is an object of the invention to describe a device for sensing a presence of at least one of the following fluids in a chemical feed tube selected from the group consisting of sanitizer, detergent and rinse agent.

It is an object of the invention to provide an oscillator section for determining an oscillating frequency and for determining a duty cycle at which the device operates.

Another object of the invention is to describe at least one frequency shaper for receiving the oscillating frequency and for converting the frequency to a square wave.

A further object of the invention is to describe at least one sensitivity element being adjustable for changing the sensitivity of the device.

It is an advantage of the invention to have at least one sensor element for sensing the presence of at least one of the following fluids in the chemical feed tube selected from the group consisting of sanitizer, detergent and rinse agent.

A further advantage of the invention is to provide an indication signal representing the sensed fluid.

Further objects and advantages of the invention will become apparent from a consideration of the drawing and ensuing description of it.

BRIEF DESCRIPTION OF THE DRAWING

The sole figure illustrates a circuit diagram of one channel for the chemical sensor of the present invention.

DESCRIPTION OF THE INVENTION

The sole figure illustrates one channel for the chemical sensor circuit 10 of the present invention. For simplicity, only one channel is shown. The actual sensor circuit board has three identical channels. The other channels utilize the same oscillator, but have separate circuits for the other sections. As is known in the art, the sections would be a sanitizer section (which is illustrated), rinse aid section, and detergent section.

The first block represents the oscillator circuit 12 of the sensor 10. The oscillator 12 consists of a comparator U2, resistors R1, R8, R9, R11, R18, R19, and a capacitor C4 as well as a diode D1. The resistors and capacitor determine the oscillator frequency and duty cycle.

The second block 14 consists of a single NAND gate U3. This gate U3 takes the output of the oscillator circuit 12 and changes the output into a square wave.

The third block 16 represents the sensitivity adjustment. This block consists simply of a potentiometer R20, and a series resistor R13 and R12. By increasing the resistance, the sensitivity increases.

The sensor element 20 is comprised of a wire wound resistor R3 which the fluid carrying tube 21 passes through. The sensor 20 operates by sensing the increase in capacitance associated with the introduction of the fluid. The figure shows both the circuit and the general shape of the wire wound tube. Like components have similar identifying numerals. The resistor R3 is only connected to the circuit at one end, therefore, the internal wire windings form one plate of the capacitor. Since the fluid forms the other plate of the capacitor and provides the AC coupled path to ground, the fluid must be conductive. For example, the sensor is not designed to sense non-conductive fluids such as distilled water.

The output of the sensor is fed into a comparator circuit 22. This comparator circuit 22 determines if the fluid is present or not. The circuit 22 comprises of two resistors R9 and R10 as well as a capacitor C9. There is also a comparator U2.

The last block output section 24 simply changes the oscillating signal from the comparator U2 into a steady DC signal to allow interface to a CMOS circuit. This output section 24 utilizes three resistors, R2 and two R9s. There is a capacitor C1, a transistor Q1, and two Schmitt-trigger inverting gates U1.

The output section 24 is connected to a switch.

The following chart list the major components for the sanitizer section illustrated and described. The other sections would utilize similar like components.

| Quantity | Reference No. | Description |
|---|---|---|
| 1 | U1 | 74HC14 HEX SCHMITT-TRIGGER |
| 1 | U2 | LM239 quad comp. |
| 1 | U3 | 74HC00 |
| 2 | R1,2 | 10k 1% res |
| 1 | R3 | 1k 20 W 5% |
| 1 | R8 | 4.7K ¼ W 5% |
| 1 | R9 | 47k 10 psip NETWORK |
| 3 | R10,11,18 | 47K ¼ W 5% |
| 2 | R12,19 | 82.5k 1% mf |
| 1 | R13 | 49.9K ⅛ W 1% |
| 1 | R20 | 50k ¼" pot |
| 1 | C1 | .01 uf cap |
| 1 | C4 | 82 pF 5% MICA |
| 1 | D1 | diode 1N4148 |
| 1 | SW1 | 4 pos dip sw |
| 1 | Q1 | npn TRANSISTOR |
| 1 | C9,10,11 | .001 uF 100 V 10% |

While the above description, contains many specificities, these should not be construed as limitations the scope of the invention, but rather as exemplification of one preferred embodiment thereof. Of course, many other variations are possible. Accordingly, the scope of the invention should be determined not by the embodiment illustrated, but by the appended claims and their legal equivalents.

We claim:

1. A device for sensing a presence of at least one of the following fluids in a chemical feed tube selected from the group consisting of sanitizer, detergent and rinse agent, said device comprising:

an oscillator section for determining an oscillating frequency and for determining a duty cycle at which said device operates;

at least one frequency shaper connected to said oscillator section, said shaper receiving the oscillating frequency and converting said frequency to a square wave:

at least one sensitivity element connected to said shaper, said sensitivity element being adjustable for changing the sensitivity of the device;

at least one sensor element connected to said sensitivity element, said sensor sensing the presence of said at least one of the following fluids in the chemical feed tube selected from the group consisting of sanitizer, detergent and rinse agent, and providing an indication signal representing said sensed fluid;

at least one comparator connected to said sensitivity element, said comparator receiving said indication signal and comparing said signal to a predetermined sequence signal, said comparator outputting a result signal based on said comparison; and at least one output section connected to said comparator, said output section receiving said result signal and changing said signal to a steady direct current signal.

2. The device of claim 1, wherein said oscillator section comprising a plurality of resistors.

3. The device of claim 1, wherein said at least one sensitivity element includes a potentiometer for adjusting the resistivity of the element.

4. The device of claim 1, wherein said at least one sensor element comprises:

a wire wound resistor positioned around the chemical feed tube; and means for sensing an increase in capacitance as the fluid flows through the chemical feed tube.

* * * * *